(12) United States Patent
DeJarnette et al.

(10) Patent No.: US 7,756,725 B2
(45) Date of Patent: Jul. 13, 2010

(54) BREAKAWAY INTERFACING OF RADIOLOGICAL IMAGES WITH WORK ORDERS

(75) Inventors: Wayne T. DeJarnette, Phoenix, MD (US); Charles D. Stockham, Clarksville, MD (US); Steven G. Wineke, Windsor Mill, MD (US)

(73) Assignee: DeJarnette Research Systems, Inc, Towson, MD (US)

( * ) Notice: Subject to any disclaimer, the term of this patent is extended or adjusted under 35 U.S.C. 154(b) by 1988 days.

(21) Appl. No.: 10/667,947

(22) Filed: Sep. 22, 2003

(65) Prior Publication Data

US 2004/0128164 A1    Jul. 1, 2004

Related U.S. Application Data

(60) Provisional application No. 60/437,556, filed on Dec. 31, 2002.

(51) Int. Cl.
*G06Q 10/00* (2006.01)
*G06F 19/00* (2006.01)

(52) U.S. Cl. .............................................. 705/2; 705/3
(58) Field of Classification Search ................. 705/2–3; 382/305, 131; 711/161; 715/783; 378/4
See application file for complete search history.

(56) References Cited

U.S. PATENT DOCUMENTS 5,452,416 A * 9/1995 Hilton et al. ................. 715/783

| | | | |
|---|---|---|---|
| 2001/0011336 A1* | 8/2001 | Sitka et al. | 711/161 |
| 2003/0228042 A1* | 12/2003 | Sinha | 382/131 |
| 2004/0086202 A1* | 5/2004 | Short et al. | 382/305 |
| 2004/0125908 A1* | 7/2004 | Cesmeli et al. | 378/4 |

* cited by examiner

*Primary Examiner*—Robert W Morgan
*Assistant Examiner*—Joseph Burgess
(74) *Attorney, Agent, or Firm*—Hodes, Pessin & Katz, P.A.

(57) ABSTRACT

A breakaway interface between radiological information systems, imaging equipment and picture archive and communications systems has automated filtering and handling of multiple study work orders or affiliated work orders, while passing single study work orders through unaltered. The work orders are processed by the breakaway interface to consolidate multiple procedure or multiple study work orders into a single super order, which is then communicated, preferably using DICOM standard protocol, to an imaging machine. The imaging machine returns a single image sequence, and the breakaway interface will then break images away from the single image sequence into a plurality of grouped image sequences. The preferred grouping is based upon anatomical regions, and separate but adjacent anatomical regions will preferably share one or more images at the boundary between the adjacent regions. The exact number of shared images may preferably be preset at the system level. A number of different techniques for analyzing the single image sequence are proposed individually or in combination, including histogram analysis, peak finding techniques, moments of order analysis, evaluating information from one or more previous analyses, and evaluating image sequence series information to distinguish discrete imaging procedures.

7 Claims, 3 Drawing Sheets

BREAKAWAY INTERFACING OF RADIOLOGICAL IMAGES WITH WORK ORDERS

CROSS REFERENCE TO RELATED APPLICATIONS

This application claims priority to U.S. provisional application Ser. No. 60/437,556 filed on Dec. 31, 2002 and incorporated herein by reference in its entirety.

BACKGROUND OF THE INVENTION

1. Field of the Invention

This invention pertains generally to computer-aided imaging systems and computer-aided radiological information systems. More specifically, the present invention incorporates image analysis and work order evaluation to ensure that a radiological information system and computer-aided imaging system produce desired and matched images and work orders in an automated and reliable manner.

2. Description of the Related Art

Radiological information systems provide a hospital, imaging or other medical facility appropriate computer software tools to manage information regarding radiological exams. Modern radiological imaging facilities will typically utilize a variety of highly sophisticated testing, imaging and analysis equipment. For exemplary purposes only, and not limited thereto, exemplary imaging equipment commonly found at such facilities may include CT, SPECT, PET, and MRI scanners. These machines are very expensive assets that will most desirably be operated in an efficient manner to minimize idle time and, simultaneously, to minimize the amount of time required to produce a desired set of images for a given patient. By minimizing the time required for a patient, the throughput on a given machine may be increased, decreasing the total cost per patient and reducing the need for additional machines that might be otherwise required to maintain a particular level of service. The patients will also see better service through reduced waiting time and fewer retakes or extra visits for missed or overlooked image requests.

The operations which are provided for through the radiological information system will typically include scheduling, billing, tracking, generation of work orders, storage of reference information such as referring physician, patient information, and the like. Such systems form an important accounting and management role within a well-managed facility and so are a vital part of the administrative data management.

In addition to the administrative scheduling and accounting functions of a typical radiological information system, additional management is required when receiving, handling and archiving radiological images. In particular, recent imaging systems are capable of generating either single images or, alternatively, a relatively large number of relatively small image slices. These slices may not be evenly distributed across a patient's body, but in accord with a physicians' needs may be unevenly concentrated in a particular body area or region. For exemplary purposes, multi-slice CT equipment is capable of producing hundreds of slices in a single very short scanning session, and the equipment is capable of scanning from the top of a person's head through the pelvis in a single acquisition. Multiple separate procedures or anatomical studies may be included in a single CT acquisition. The maintenance of this image data, which generally involves the archiving of large amounts of data, is most preferably handled through specialized computer systems referred to herein as Picture Archive and Communication Systems (PACS). A PACS system will most desirably incorporate much specialized software which enables specialized handling and display of the images, and will most preferably work cooperatively as a part of or in close association with the radiological information system.

Unfortunately, the objectives of the various systems are somewhat different from each other, and, as a result, certain technical challenges are present in the integration of the various components that comprise a complete radiological program. For example, to facilitate billing most radiological information systems require a specific work order be associated with each image set. That way, there is a clear accounting trail of work ordered and delivered, and the system can thereby ensure that the orders have properly been fulfilled and billed. This approach works very well for single study work orders. The work order may be generated without intelligent intervention, and the radiology technician can conduct the single study as ordered. When complete, the radiologist will generate a single radiology report and the facility will then deliver and bill for the study.

Unfortunately, when there is a multi-anatomical study or multi-procedure study work order placed, which is very well handled by many axial medical imaging scanners, neither the PACS system nor the radiological information system are well suited. Prior to the present invention, the persons entering or tracking the information would be called upon to recognize that the request was for a plurality of studies. In order for the radiological information system and the PACS to accurately account for this multi-study, a person would have to enter the work order manually by dividing the work order into a plurality of work orders. When the work order was not divided and manually entered, only one imaging study could be assigned to or electronically associated with the work order. Not only is a radiological information system designed to account for each study separately, but the PACS associates only one procedure with the study. Consequently, for a multi-anatomical study, the remaining image studies could not be assigned by the reading radiologist, and these studies remained unassigned and not associated with any particular work order. As a result, the facility was unable to properly account, track and bill for the remaining image studies.

As aforementioned, the prior art manual intervention is not limited solely to the entry of information into the radiological information system. Once the multi-study is properly entered into the radiological information system, including dividing into each individual study, the work order is conveyed to a technician responsible for conducting a particular study. In the case of a multi-anatomical study, such as for exemplary purposes only and not limiting thereto, a CT scan covering head, neck and upper torso, the CT technician will most desirably recognize that the patient can be positioned for a single comprehensive procedure. The work orders, however, indicate three separate procedures, a discrepancy that may, particularly in the case of a new or less-experienced technician, lead to error, confusion or delay, any of which is associated with a decreased level of service and the potential need to expose the patient multiple times to the imaging radiant energy.

When the CT technician properly completes the single comprehensive procedure, yet another problem exists. The work order has multiple studies specified, and yet there is only a single imaging sequence produced by the imaging equipment. Consequently, interpretation and manual intervention are once again required. This time, the technician must review the images and determine an appropriate grouping to correspond to the work order, or a radiologist or the like will otherwise have to re-organize the single multi-study output from the equipment to attempt to match the studies to the multiple work orders. In either case, additional work not associated directly with patient care is undesirably required.

In the event the multi-study imaging output is not divided (which is tedious work not directly affiliated with patient care) issues arise regarding the accounting between the radiology report and the radiological information system. When work orders are properly divided, but the images are not, the remaining work orders are all too frequently orphaned, unmatched to any image set in spite of the fact that the imaging study has actually been completed.

In either case, when work orders are not properly divided or images are not properly divided, another very significant benefit of the PACS is lost. By electronically archiving imaging information, a radiologist or other health care provider may compare present images to past images stored with the patient's records, and do this with almost no delay. Unfortunately, when either the work order or the imaging studies have not been properly manually divided, the physician will find it difficult or impossible to locate the archived images to carry out the past and present comparisons. For example, if the patient had a full scan including head, neck and upper torso as described above, and the results of the head scan were not stored with the head scan work order, the physician may be unable to locate the head scan, and may typically assume that it has been permanently lost or destroyed or waste valuable time researching what should be an automatic display. Many PACS systems refer to studies by procedure type, so it is important that distinct procedures be subdivided, or the information from the procedure may not be retrievable using the procedure type reference. As may be understood, comparisons of current imaging information with previous imaging data can be invaluable in the evaluation and diagnosis of a medical condition, and the loss of such useful information can be very detrimental to the provision of timely and efficient patient care.

What is desired then is a system which eliminates the tedious and unreliable manual intervention, and thereby allows the users of each system to better focus their efforts on their primary duties.

SUMMARY OF THE INVENTION

The present invention provides, for use in combination with medical imaging equipment normally operating independently of a stand-alone radiological information system, a breakaway interface disposed between the radiological information system and PACS and the medical imaging equipment. This breakaway interface facilitates conventional use of the medical imaging equipment for multi-anatomical or multi-procedural studies for generating a series of anatomical images under a single work order and for simultaneously producing respective individual work orders which are matched to corresponding anatomical images, and which are inputted into the radiological information system for management control, tracking, accounting and/or billing purposes.

Preferably, a picture archive and communication system (PACS) is provided for transmitting individual work orders and storing the anatomical images into the PACS.

In a first manifestation, the breakaway interface is operative between a radiology accounting and billing information system having one-to-one correspondence between individual radiological studies and individual work orders, a picture archive and communication system (PACS) having one-to-one correspondence between individual radiological studies and individual work orders, and a radiological imaging machine that produces multiple studies from a single work order. Means are provided within the breakaway interface for receiving an image sequence from the radiological imaging machine. Means are also provided for dividing the image sequence into separate, anatomically associated image sequences. Means are additionally provided for matching anatomically associated images with corresponding individual work orders. Additional means transmit the matched anatomically associated image sequences and corresponding individual work orders to the picture archive and communication system.

In a second manifestation, the invention is a method of separating a single radiological image sequence comprising a plurality of individual radiological images into a plurality of sequences and associating the plurality of sequences with a plurality of associated studies and work orders. According to the method, the single radiological image sequence is received in electronic form. Individual radiological images within the sequence are analyzed, preferably using histogram analysis, moments of order analysis and peak finding techniques, info from previous analysis steps, and the evaluation of series information to distinguish between multiple procedures, to determine an associated anatomical region. The individual radiological images are assigned to an appropriate one of the plurality of associated studies and work orders based upon the analysis and determination.

In a third manifestation, the invention is a method of processing radiological orders using a radiological information system containing radiological examination orders and associated information, a picture archive and communication system, and an imaging apparatus capable of producing an image sequence having a plurality of individual images therein, including interfacing the radiological information system, the picture archive and communication system and the imaging apparatus in an effective and efficient manner. According to the method, examination orders are received from the radiological information system, and then distinguished by whether the orders are unaffiliated with other examination orders or not. Affiliated examination orders are assembled into a super order. Unaffiliated examination orders and super orders are conveyed to the imaging apparatus for imaging, which will generate image sequences having at least one individual radiological image corresponding to unaffiliated examination orders and super orders. The image sequences corresponding to unaffiliated examination orders are delivered to the picture archive and communication system without further processing. Images within image sequences corresponding to super orders are analyzed, preferably using histogram analysis and peak finding techniques, information from previous analysis steps, and by evaluating series info to distinguish multiple procedures, to determine an associated anatomical region. Based upon the analyzing and determining, individual radiological images are assigned to an appropriate one of the associated studies and work orders. Finally, individual radiological images and associated studies and work orders are transmitted to the picture archive and communication system for further processing.

OBJECTS OF THE INVENTION

A first object of the invention is to provide improved and more highly automated communication between a radiological information system and a radiological imaging machine. A second object of the invention is to reduce the need for human intervention and interpretation, and consequently reduce the likelihood for errors. A third object of the invention is to ensure that appropriate information is stored with each appropriate work order, whereby at a later date the imaging information may be readily obtained for review and comparison. A fourth object of the invention is to permit both a radiological information system and a radiological imaging machine to be operated using native logic and associated work orders, whereby the benefits of each system are preserved and allowed to remain optimal for their intended purposes. Another object of the invention is to provide filtered conversions both from a radiological information system to a radiological imaging machine and in an opposite direction from said radiological imaging machine to said radiological information system. A further object of the invention is to maintain compliance with existing standards, such as the DICOM standards. These and other objects are achieved in the present invention, which may be best understood by the following detailed description and drawing of the preferred embodiment.

DESCRIPTION OF THE PREFERRED EMBODIMENT

Figure 1:
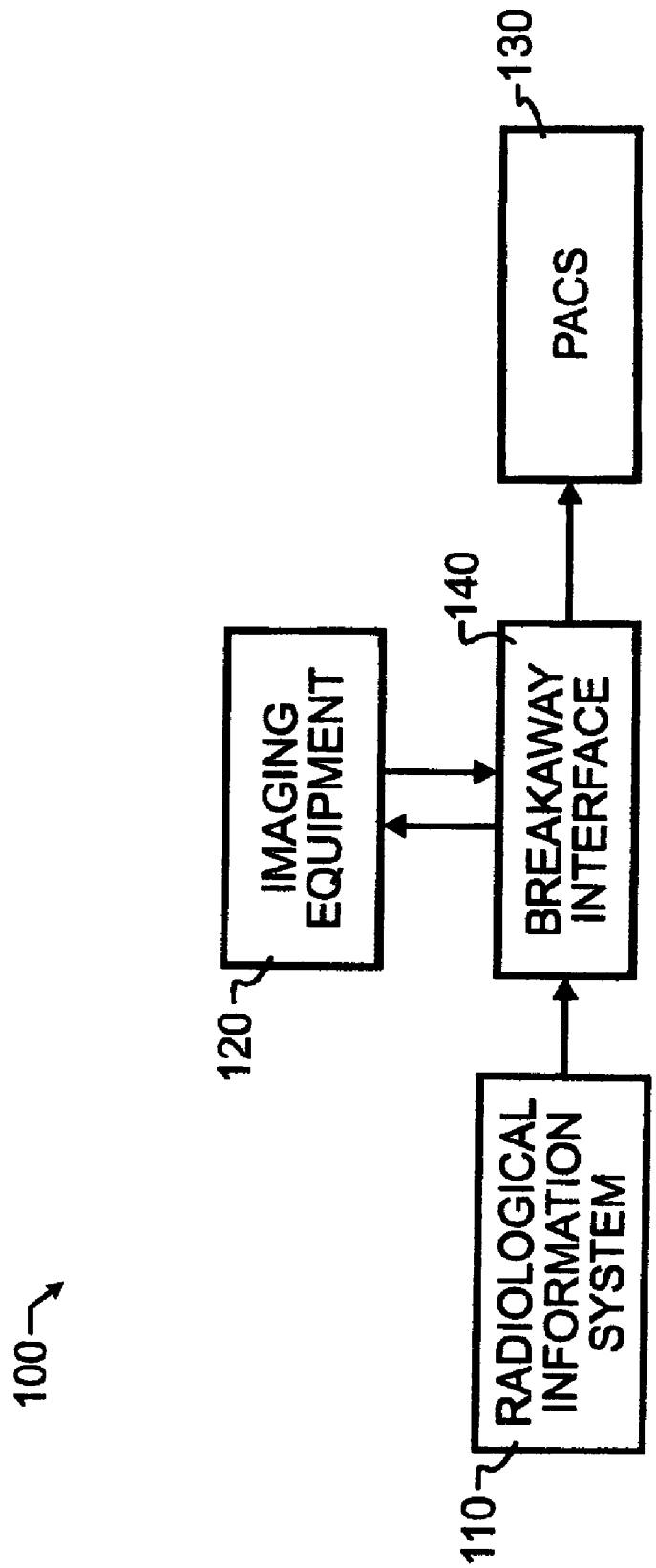
FIG. 1 illustrates the preferred breakaway interface and associated imaging systems designed in accord with the teachings of the present invention by schematic block diagram.
Figure 2:
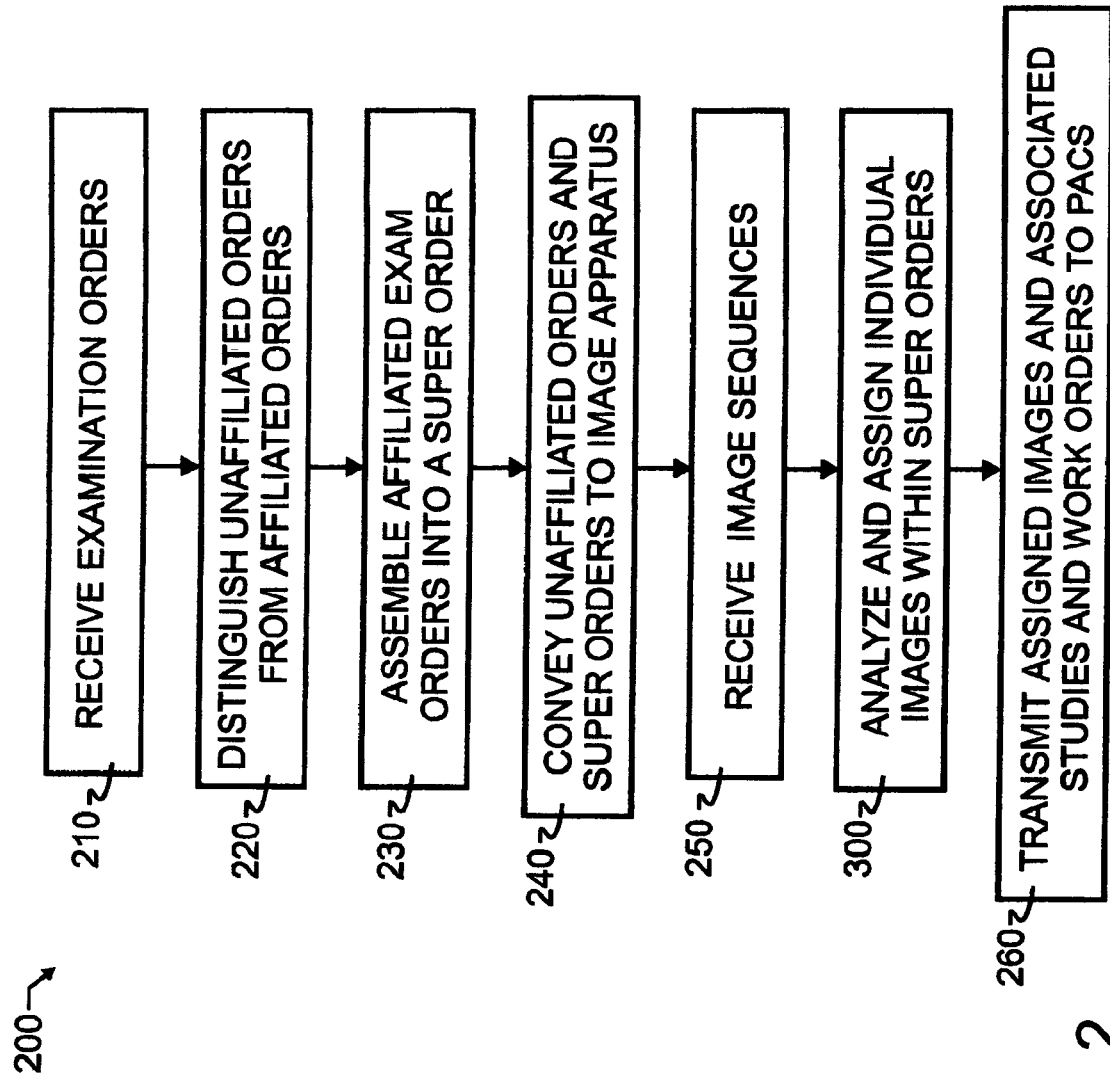
FIG. 2 illustrates the preferred method of processing radiological orders, using the preferred method of breaking away images shown in FIG. 3, in accord with the teachings of the present invention by flow chart.
Figure 3:
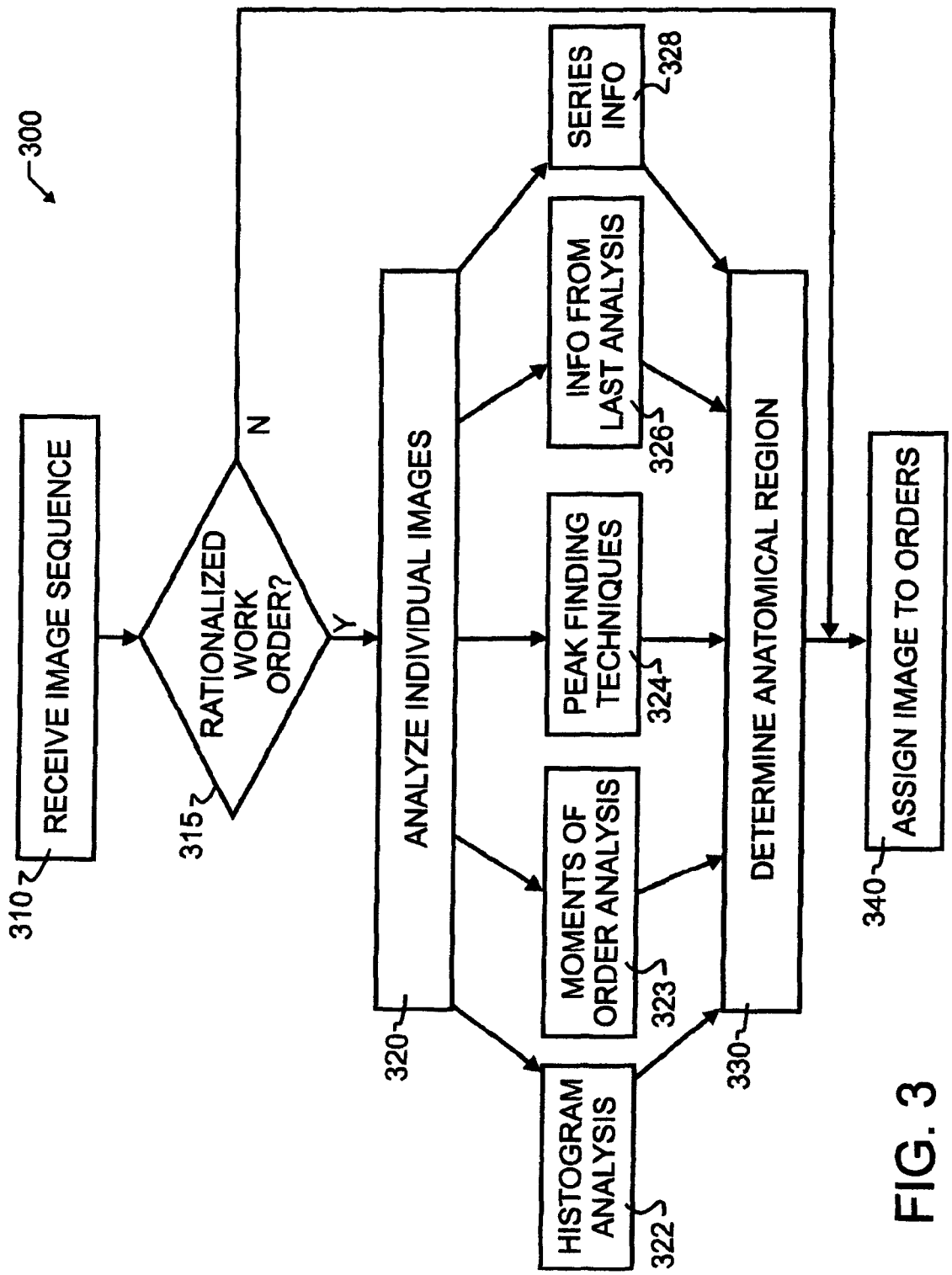
FIG. 3 illustrates the preferred method of breaking images away from a multi-study image sequence into individual anatomically organized image sequences in accord with the teachings of the present invention by flow chart.

A preferred embodiment breakaway apparatus 100 and breakaway method 200 of interfacing radiological images with work orders is illustrated in FIGS. 1-3. As illustrated in FIG. 1, breakaway apparatus 100 couples a standard radiological information system 110 or other known or suitable substitute, including a PACS system, to breakaway interface 140. In the preferred embodiment, radiological information system 110 will communicate to breakaway interface 140 by transmission of communications signals using industry standard protocols such as DICOM work lists or HL-7 orders.

Most preferably, though not essential to the workings of the present invention, the various components within breakaway apparatus 100 will be compliant with the DICOM industry standards. DICOM, which stands for Digital Imaging and Communications in Medicine, is the industry standard for transfer of radiological images and other medical information between computers. Patterned after the Open System Interconnection of the International Standards Organization, DICOM enables digital communication between radiological imaging equipment and systems from various manufacturers.

Compliance with the DICOM open standards is important to ensure compatibility between radiological services providers and various health-care facilities that may be physically separated one from the other. The facilities may be divided merely within buildings, or across distant geographic regions. Hardware and software from diverse vendors located at one site or many remote sites can communicate by means of the DICOM standard across an open system network. As a result, medical images can be captured and communicated more quickly, allowing physicians to make diagnoses sooner. Additionally, the use of DICOM standard components ensures more modularity in the construction of the preferred embodiment. Consequently, for the purposes of this disclosure, phrases such as coupling, transmitting, receiving and the like will be understood to include not only direct connection by local wiring, but also to other suitable communications, including but not limited to both physical and virtual interconnections including local area networks, wide area networks, Internet, radio and satellite communications, and so forth.

Breakaway interface 140 includes means to receive the work lists, the means which are dependent upon the type of network or communications system in use and which includes all suitable known apparatus. The reception means, for exemplary and not limiting purposes, may include such devices as network interface cards, modems, direct wiring or the like, typically associated with appropriate software or hardware for implementing the necessary function. The appropriate apparatus will be determined by those skilled in the art at the time of design.

Breakaway interface 140 will filter work lists or orders received from radiological information system 110, as will be described in much greater detail with regard to FIGS. 2 and 3 herein below, and then transmits a rationalized work list, preferably using the DICOM standards and format, to imaging equipment 120. Similar to the above mentioned reception means, breakaway interface 140 will include appropriate means for transmission, once again dependent upon the type of network or communications system, and once again determined by those skilled in the art at design time.

Imaging equipment 120 may include one or more of a wide variety of diverse medical imaging equipment. The invention is believed to offer significant benefit and advantage when applied more particularly to axial medical imaging equipment, and most particularly to such equipment when the equipment is capable of generating many image slices within a very short period of time, or processing large body sections or separate anatomical studies at once. Exemplary are current multi-slice CT scanners, which are capable of producing hundreds of slices in a short time interval, scanning from the top of a head through the pelvis in a single acquisition, and processing images for five separate anatomical studies in a single CT sequence. Capabilities to which the present invention is most suited may also be found in many SPECT, PET and MRI imaging machines, though this list is strictly exemplary, and in no way limiting to the scope of the invention.

Imaging equipment 120 in turn transmits back to breakaway interface 140 an image sequence taken in accord with the rationalized DICOM work list. Once again, the image sequence will preferably be transmitted from imaging equipment 120 to breakaway interface 140 in accord with the DICOM standards, though the invention is not so limited. Breakaway interface 140 will include reception means suited for receiving image sequences from imaging equipment 120, such means within the purview of those skilled in the art and the selection of which will be made at design time.

In the event the image sequence was generated from a rationalized work list which was different from the work list received from radiological information system 110, breakaway interface 140 will include means to break images away from the image sequence received from imaging equipment 120 into smaller rationalized image sequences. In the preferred embodiment, breakaway interface 140 intelligently applies algorithms to the images to determine the best way to split up the image sequence, as will be described in greater detail herein below with specific reference to FIG. 2.

Once the smaller rationalized image sequences are derived from the larger sequence received from imaging equipment 120, breakaway interface 140 includes means to communicate the smaller rationalized image sequences to a PACS system 130 or the like. Most preferably, the communications protocol will conform to DICOM standards, though this is not essential to the workings of the invention. In addition to the transmission of the rationalized image sequences, the associations to rationalized work lists or EL-7 orders will also be transmitted, thereby ensuring proper one-to-one correspondence within PACS 130. The specific apparatus used will be selected by those skilled in the art from the myriad of available hardware and software combinations known in the art to be suitable for the communications required herein.

In accord with the teachings of the present invention, the provision of breakaway interface 140 enables users of radiological information system 110 and picture archive and storage system 130 to continue to generate work orders, bills, studies, archival records and the like using the systems as they were designed, with one-to-one work order to image sequence and study correspondence, without special training or manual intervention for exceptions such as multiple procedure studies or multiple-study imaging. This conformance is highly desirable, since these systems were designed to best ensure accurate and optimal management, tracking, and archival retrieval. The avoidance of manual interventions for exceptions is also highly desirable, since, as aforementioned, such manual intervention is extremely tedious, prone to errors, and very much avoided in industry, to the point of seriously hampering the effectiveness of entire electronic radiology systems.

The input to imaging equipment 120 is additionally optimized by breakaway interface 140, assembling super orders where appropriate, thereby reducing the clutter of pluralities of work orders for a single scanning sequence, and also eliminating the need for manual intervention to recognize and assemble the plurality of work orders into the single scanning sequence. Consequently, not only are the operations at the radiological information system 110 and PACS 130 optimized, but so is the operation of imaging equipment 120.

FIG. 2 illustrates a preferred method 200 of processing radiological orders within breakaway interface 140. Method 200 may be implemented using various combinations of software and hardware, as is known in the art. Consequently, method 200 is not limited solely to either software or hardware, and may include one or both in combination. Breakaway interface 140 must receive examination orders at step 210. These examination orders will typically be provided through radiological information system 110, but may alternatively be permitted to be received from other diverse systems or sources, including but not limited to PACS 130 or other remote radiological information systems, PACS, or other systems or sources capable of providing sufficient information for breakaway interface 140 to generate or assemble appropriate examination orders.

Any orders that are affiliated with or would require additional work orders, for example multiple studies or procedures on a single patient using a single imaging machine, will preferably be distinguished and assembled into a super order for that machine, as shown in steps 220 and 230. Unaffiliated orders are conveyed to imaging equipment 120 as received, while affiliated orders are collected in step 230 and conveyed as a single super order to imaging equipment 120 in step 240. This conversion of work orders into rationalized work orders at step 230 is done by breakaway interface 140, where rationalized work orders refer to super orders that are either assembled by or alternatively identified as multiple procedure or multiple study work orders by breakaway interface 140.

Imaging equipment 120 will generate one or more image sequences, which in turn are received at breakaway interface 140 in step 250. These received image sequences are then analyzed and assigned as outlined herein below with reference to method 300. The assigned images and associated studies and work orders are then preferably transmitted to PACS 130 as shown by step 260, though transmission to other devices and equipment available either directly or through a network or other diverse communication channel may be used. Among the possible devices for transmission to, but not limiting the invention to the present list, are PACS systems, medical imaging networks, radiological information systems, and various storage devices for possible future use or reference.

FIG. 3 illustrates the preferred method 300 of identification of the appropriate divisions between various smaller rationalized image sequences. In the preferred embodiment breakaway apparatus 100, method 300 is the preferred means for dividing the image sequence into separate, anatomically associated image sequences. At step 310, an image sequence is received from imaging equipment 120. A decision must be made at step 315 to decide whether the work order was rationalized or not. This decision may, for exemplary purposes, be made by tracking within breakaway interface 140 the work orders and whether they were rationalized. In the event the work order was not a rationalized work order, meaning the image sequence and work order have the desired one-to-one correspondence, then the image may be directly assigned to the order at step 340.

For rationalized work orders, individual images within an image sequence will be analyzed beginning at step 320. As is schematically illustrated, this image analysis may include one or more techniques, either simultaneously or separately. Most preferred techniques include image pixel analysis using histograms analysis, moments of order analysis, and peak finding techniques at steps 322, 323 and 324, and will also include comparisons of the last image analysis in step 326 and review of series information at step 328. Histogram analysis, moments of order analysis and peak finding techniques for pixel analysis are known in the graphics industry, and the application within the present breakaway interface 140 will be within the skill of those working in the present industry upon a review of the present disclosure and without further unnecessary elaboration. While several preferred image analysis techniques are described herein, other image analysis techniques may be used or adapted for application herewith based upon the goals apparent from the present disclosure, and consequently without deviating from the present disclosure. In fact, owing in part to the great flexibility of the present invention, as image analysis techniques are introduced or refined, they will reasonably be expected to be implemented in combination with the other features disclosed herein without departing from the scope of the present invention.

Information from the last analysis, as shown in step 326, represents an awareness by the present inventors that there is a sequence which various image slices must occur in. In other words, a person's head is above the neck which in turn is above the chest. Consequently, if the last image represented a neck region image, and the imaging is proceeding from top of the head downward toward the pelvis, then the current image could not reasonably be taken from the head. Step 326 is not limited solely to the last image that was analyzed, but may alternatively represent the last state of the complete sequence analysis as well, depending upon data storage and processing capabilities designed into breakaway interface 140.

Series information as shown in step 328 represents a check to see if the current image is from the same image series and frame of reference as the previous image. As an example, it is possible that a single image sequence may include head and neck slices as a first procedure executed by the imaging equipment 120 and represented by a first series designation, and then also include a second imaging procedure executed by imaging equipment 120 showing chest, abdomen and pelvis slices. In such an instance, breakaway interface 140 will most preferably recognize that the series information creates a logical separation of the image sequence into distinct anatomical regions. Consequently, in such an instance, one or more of the boundaries of division between smaller rationalized image sequences may be defined entirely by a change in image series information.

As already noted herein above, the specific techniques for analyzing individual images will vary from one system to another. The present invention uses all five steps 322-328 in the analysis, though other systems may include any combination of steps 322-328 in any order or simultaneously, or other image analysis techniques.

From the analysis of steps 320-328, breakaway interface 140 is preferably programmed to determine what anatomical region the individual image was taken from. Once determination step 330 has been completed, the individual image may be confidently assigned to one or more orders in step 340. Preferably, at the boundaries of divisions between smaller rationalized image sequences, and where the divisions are not occurring due to changes in series described with reference to step 328, images will be assigned so as to overlap between both of the adjoining sections. Said another way, images may be duplicated between two smaller rationalized image sequences in order to adequately preserve all of the important features found near the boundaries of each separate image sequence. The amount of overlap between smaller rationalized image sequences may be selected or configured by the user in the preferred embodiment, though this is not essential to the working of the invention.

In accord with the preferred embodiment methods 200 and 300 illustrated in FIGS. 2 and 3 and described in detail herein above, the present invention performs automatic dissection of a single, multi-order image study into its constituent studies. This processing occurs without a user or the PACS needing to intervene, or even needing to be aware of the automatic intervention and dissection.

Having thus disclosed the preferred embodiment and some alternatives to the preferred embodiment, additional possibilities and applications will become apparent to those skilled in the art without undue effort or experimentation. Therefore, while the foregoing details what is felt to be the preferred embodiment of the invention, no material limitations to the scope of the claimed invention are intended. Further, features and design alternatives that would be obvious to one of ordinary skill in the art are considered to be incorporated herein. As but one example and certainly not limiting of the possibilities, while breakaway interface 140 is illustrated and described herein above as a separate apparatus, those skilled in the art will recognize that the function of breakaway interface 140 may be implemented independently of physical placement. In other words, breakaway interface 140 may be included within or implemented in any of the remaining associated components, such as, for example, the imaging equipment 120, without negating the functional characteristics described herein above. Where one or more of the components 110-130 have sufficient computational power and storage, only software appropriate to the machine may be required to implement the present invention Consequently, rather than being limited strictly to the features recited with regard to the preferred embodiment, the scope of the invention is set forth and particularly described in the claims herein below.

We claim:

1. A method of processing radiological orders using a radiological information system containing radiological examination orders and associated information, a picture archive and communication system, and an imaging apparatus capable of producing an image sequence having a plurality of individual images therein, including interfacing said radiological information system, said picture archive and communication system and said imaging apparatus in an effective and efficient manner, comprising the steps of:

receiving said radiological examination orders;

affiliating said radiological orders using said imaging apparatus that are each assigned to a common patient into a super order;

conveying said radiological examination orders to said imaging apparatus for imaging;

generating image sequences having at least one individual radiological image;

delivering image sequences corresponding to unaffiliated radiological examination orders to a storage system;

analyzing said at least one individual radiological image within said image sequences corresponding to said super orders using automated electronic image analysis comprising histogram analysis, moments of order analysis, and peak finding techniques to determine associated ones of said radiological orders;

assigning said at least one individual radiological image to an appropriate one of said plurality of associated studies and work orders based upon said analyzing and determining step; and transmitting said assigned at least one individual radiological image and said appropriate one of said plurality of associated studies and work orders to said storage system.

2. The method of processing radiological orders of claim 1 wherein said step of affiliating further comprises the steps of:

distinguishing said radiological examination orders that are unaffiliated with other radiological examination orders from radiological examination orders that are affiliated with other radiological examination orders; and assembling affiliated radiological examination orders into a super order responsive to said distinguishing.

3. The method of processing radiological orders of claim 2 wherein:

said conveying step further comprising conveying said unaffiliated radiological examination orders and said super orders to said imaging apparatus for imaging responsive to said distinguishing and said assembling steps; and said at least one individual radiological image is generated corresponding to said unaffiliated radiological examination orders and said super orders.

4. The method of processing radiological orders of claim 2 wherein said radiological examination orders are received from said radiological information system;

said image sequences and said unaffiliated radiological examination orders are delivered to said picture archive and communication system; and said at least one individual radiological image and said appropriate one of said plurality of associated studies and work orders are transmitted to said picture archive and communication system.

5. The method of processing radiological orders of claim 1 wherein said analyzing step further comprises analysis of information from at least one previous analysis step.

6. The method of processing radiological orders of claim 1 wherein said analyzing step further comprises evaluating series information to distinguish multiple procedures.

7. The method of processing radiological orders of claim 1 wherein said step of determining an associated region further comprises determining an associated anatomical region.

\* \* \* \* \*